United States Patent [19]
Suzuki et al.

[11] Patent Number: 5,843,670
[45] Date of Patent: Dec. 1, 1998

[54] CARBODIIMIDE GROUP-CONTAINING DIGOXIGENIN DERIVATIVES

[75] Inventors: Osamu Suzuki; Gen Masuda; Namiko Shiohata; Kazuko Matsumoto, all of Tokyo, Japan

[73] Assignee: Nisshinbo Industries, Inc., Japan

[21] Appl. No.: 837,853

[22] Filed: Apr. 22, 1997

[30] Foreign Application Priority Data

May 8, 1996 [JP] Japan .................................... 8-113922

[51] Int. Cl.⁶ .............................. C12Q 1/68; C07J 19/00
[52] U.S. Cl. ........................ 435/6; 536/5; 540/2; 552/502
[58] Field of Search .................... 536/5; 540/2; 552/502; 435/6

Primary Examiner—Ardin H. Marschel
Assistant Examiner—Jezia Riley
Attorney, Agent, or Firm—Jones & Askew

[57] ABSTRACT

As a novel digoxigenin derivative which makes the labeling procedure simple, can be used to label a naturally-occurring nucleic acid, and enables highly sensitive assay, carbodiimide group-containing digoxigenin derivative represented by the following formula is used as the label in a nucleic acid detection method or immunoassay.

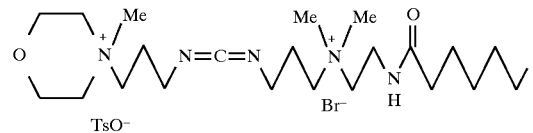

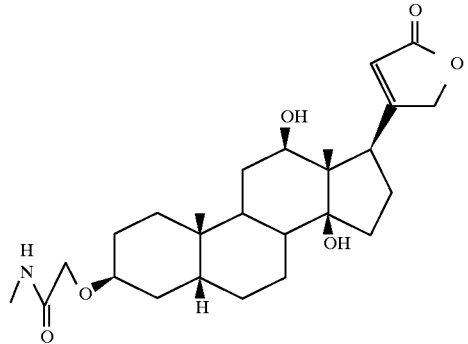

8 Claims, No Drawings

CARBODIIMIDE GROUP-CONTAINING DIGOXIGENIN DERIVATIVES

FIELD OF THE INVENTION

The present invention relates to a novel digoxigenin derivative. More specifically, the present invention relates to a novel digoxigenin derivative having high sensitivity and capable of labeling a nucleic acid or a protein easily, a process for producing it, and a detection method using it.

BACKGROUND OF THE INVENTION

Conventionally, radioactive isotopes (e.g., $^{32}P$, $^{14}C$, $^{3}H$, etc.) have been used for labeling a nucleic acid incorporating them into the nucleic acid by means of the nick translation method, the random primer method, the tailing method, and the like. The detection method using such a radioactive isotope-labelled nucleic acid is generally characterized by high sensitivity and high specificity, while it is disadvantageous in safety, expense, and stability. Namely, radioisotopes must be preserved and used taking their half-life period into consideration. In other words, they cannot be preserved for a long time and cannot be used repeatedly. Further, since they are generally harmful to humans, the strict care must be taken in handling them, for example, by using specific facilities.

For these reasons, labeling of a nucleic acid and a protein with a non-radioactive substance has been increasingly used. Particularly, the method using biotin having high affinity for avidin or streptoavidin has been widely used. The method can be carried out by binding an enzyme-labelled avidin to biotin which is incorporated into a nucleic acid and, then measuring activity of the bound enzyme. However, such a biotin-labeling method has problems that it requires complicated operation, specific reaction devices or conditions, and a lot of time for labeling procedure.

On the other hand, digoxigenin derivatives having a basic skeleton of digoxigenin to which another molecule or carrier is bound are used as assay reagents in various biological analyses. For example, a digoxigenin derivative is used for measuring a cardiac aminosugar, particularly digoxin, in immunoassay as an antibody specific to the cardiac aminosugar. Also, in a nucleic acid-detection method using a nucleic acid having a complementary base sequence to which hapten is bound as the label, a digoxigenin derivative is used as the hapten. These assays are carried out based on the principle of interaction between hapten and antihapten antibody. As such haptens, the digoxigenin derivative, in which digoxigenin is bound to another molecule via the 3-position of the steroid skeleton, is generally used.

However, the digoxigenin derivatives which have been conventionally used have the following disadvantages. Namely, a digoxigenin derivative in which the steroid skeleton of digoxigenin is bound to another molecule via an ester bond or a urethane bond has a problem that it is decomposed during its use since the ester bond or the urethane bond is extremely unstable under basic conditions to easily undergo hydrolysis.

Further, the digoxigenin derivative has a reactive hydroxyl group at the 12-position of the steroid skeleton as well as at the 3-position. Thus, upon synthesis of the derivative, a mixture of the 3-derivative and the 12-derivative is often produced. If such a mixture is used without carrying out purification, accuracy of the assay is reduced because of errors. On the other hand, there is a problem that separation of the mixture into the respective isomers requires a great expense. Further, the digoxigenin derivative may possibly be contaminated with a variant, for example, in which an oxygen atom at the 3-position of the steroid skeleton is replaced with a nitrogen atom of an amino group. Such a variant sometimes prevents an antibody to non-variant steroid skeleton from recognizing a hapten.

In order to solve the above problems, a digoxigenin derivative in which the steroid skeleton is bound to another molecule at the 3-position via an ether bond has been proposed as a substitute (see JP-B-6-37513). However, since this derivative is designed to have a group reactive with an amino group at the side chain extended from digoxigenin, it must be reacted to label a nucleic acid which has been artificially modified with an amino linker and the like. Thus, there are problems that the labeling procedure is complicated and it cannot be used to label a naturally-occurring DNA.

SUMMARY OF THE INVENTION

An object of the invention is to provide a novel digoxigenin derivative to be used as a label in a nucleic acid detection method or immunoassay, which makes the labeling procedure simple, can be used to label a naturally-occurring nucleic acid, and enables highly sensitive assay.

It is known that a carbodiimide compound reacts with an nucleic acid. For example, it is reported that a carbodiimide compound reacts with guanine and thymine which do not form a hydrogen bond in a nucleic acid, to form an addition product [P. T. Gilham, J. Amer. Chem. Soc., 84, 688 (1962)].

As a result of intensive investigation of a method of simply and efficiently introducing digoxigenin into a nucleic acid, a protein and the like, the present inventors found that the above problems can be solved by introducing a digoxigenin moiety to a carbodiimide compound utilizing high reactivity of a carbodiimide moiety with a nucleic acid or a protein, to thereby achieve the present invention.

The present invention provides a carbodiimide group-containing digoxigenin derivative represented by the following formula (I):

$$B—Y^2—N=C=N—Y^1—W—Z \quad\quad (I)$$

wherein Z represents a digoxigenin-containing moiety represented by the following formula (Z):

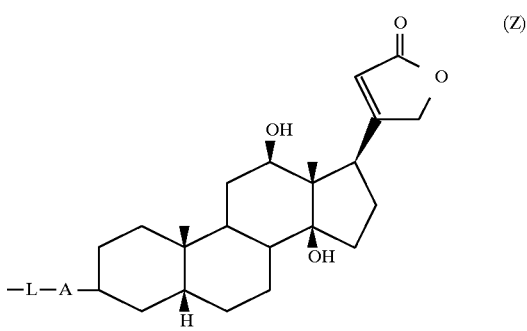

wherein A represents —O—, —COO—, or —NHCOO—;

L represents a straight-chain or branched alkylene group which may have a moiety in the main chain selected from the group consisting of —NHCO—, —CONH—, —O—, —S—, —NR—, wherein R is an alkyl group, —COO—, and —OCO—;

W represents a quaternary ammonium group;

$Y^1$ and $Y^2$ each represents a direct bond or a straight-chain or branched alkylene group having from 1 to 20 carbon atoms in its main chain and optionally having in the main chain a moiety selected from the group consisting of —NHCO—, —CONH—, —O—, —S—, —NR—, wherein R is an alkyl group, —COO—, and —OCO—; and B represents a hydrogen atom or a monovalent organic group which may be the same as or different from that represented by —W—Z.

The present invention also provides a carbodiimide-containing digoxigenin derivative represented by the above formula (I) in which W is a quaternary ammonium group represented by the following formula (W):

wherein $R^1$ and $R^2$ each represents a straight-chain or branched, saturated or unsaturated aliphatic hydrocarbon group having from 1 to 6 carbon atoms, a substituted or unsubstituted cycloalkyl group, a substituted or unsubstituted aryl group, a substituted or unsubstituted aralkyl group, or a nitrogen-containing heterocyclic group formed by $R^1$ and $R^2$ which are bound to each other; and X represents a halogen atom.

The present invention also provides a carbodiimide group-containing digoxigenin derivative represented by the above formula (I) in which B represents a tertiary amino group or a quaternary ammonium group.

The present invention also provides a carbodiimide group-containing digoxigenin derivative represented by the above formula (I) in which B is a monovalent organic group represented by —W—Z, wherein W and Z each has the same definition as in the formula (I).

The present invention also provides a carbodiimide group-containing digoxigenin derivative represented by the above formula (I) which is a compound represented by the following formula (II):

aralkyl group, or a nitrogen-containing heterocyclic group formed by $R^1$ and $R^2$ which are bound to each other;

and

X represents a halogen atom.

Further, the present invention provides a process for producing the above-described carbodiimide group-containing digoxigenin derivative which comprises a step of reacting a carbodiimide compound represented by the following formula (III):

$$B—Y^2—N=C=N—Y^1—W' \qquad (III)$$

wherein B, $Y^1$ and $Y^2$ each has the same meaning as those defined in the formula (I) and W' represents a substituted or unsubstituted amino group, with a digoxigenin halide represented by the following formula (IV):

$$Z—X \qquad (IV)$$

wherein Z has the same meaning as that defined in the formula (I); and X represents a halogen atom.

Furthermore, the present invention relates to a method of detecting a nucleic acid by hybridization using the labelled nucleic acid, wherein the above-described carbodiimide group-containing digoxigenin derivative is used as the label.

Moreover, the present invention relates to a method of immunoassay using a labelled antigen or a labelled antibody, wherein the above-described carbodiimide group-containing digoxigenin derivative is used as the label.

The digoxigenin derivative represented by the formula (I) according to the present invention is a compound having a carbodiimide group which is highly reactive with a nucleic acid base, and digoxigenin which is known to have highly sensitive reactivity in the assay. It enables labeling of a naturally-occurring DNA by a simple method without using a nucleic acid artificially modified with an amino linker and the like. It can be handled simply as compared with photoreactive labeling compounds. Therefore, it is useful as the label for introducing a digoxigenin moiety to a nucleic acid or a protein.

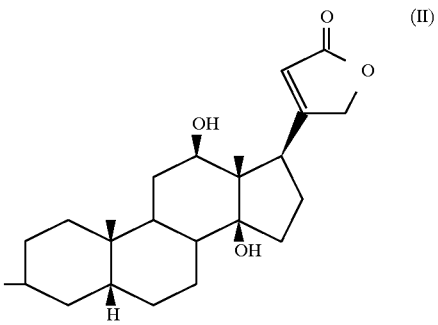

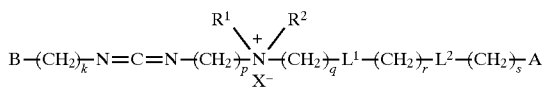

wherein k, p, q, r and s each represents an integer of from 1 to 12;

$L^1$ and $L^2$ each represents a moiety selected from the group consisting of —NHCO—, —CONH—, —O—, —S—, —NR—, wherein R is an alkyl group, —COO—, and —OCO—;

A and B each has the same meaning as those defined in the formulae (I) and (Z);

$R^1$ and $R^2$ each represents a straight-chain or branched, saturated or unsaturated aliphatic hydrocarbon group having from 1 to 6 carbon atoms, a substituted or unsubstituted cycloalkyl group, a substituted or unsubstituted aryl group, a substituted or unsubstituted

DETAILED DESCRIPTION OF THE INVENTION

The embodiments of the present invention will be illustrated in detail below.

(1) Carbodiimide group-containing digoxigenin derivative of the invention

The carbodiimide group-containing digoxigenin derivative according to the present invention has the structure represented by the above formula (I). In the formula (I), Z represents a digoxigenin-containing moiety represented by the formula (Z), and W represents a quaternary ammonium group. $Y^1$ and $Y^2$ each represents a direct bond or a straight-chain or branched alkylene group having from 1 to 20 carbon atoms in the straight-chain or the main chain which may have in the main chain a moiety selected from the group consisting of —NHCO—, —CONH—, —O—, —S—, —NR—, wherein R is an alkyl group, —COO—, and —OCO—. B is a hydrogen atom or a monovalent organic group which may be the same as or different from —W—Z in the formula (I).

In the formula (Z), A represents —O—, —COO—, or —NHCOO—, preferably —O—. L represents a straight-chain or branched alkylene group which may have in the main chain a moiety selected from the group consisting of —NHCO—, —CONH—, —O—, —S—, —NR—, wherein R is an alkyl group, —COO—, and —OCO—. The main chain of L has preferably from 1 to 20 carbon atoms. Specifically, L is exemplified by an alkylene group represented by the following formula (L):

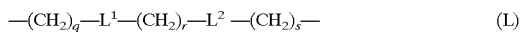

In the formula (L), q, r ,and s each represents an integer of from 1 to 12. $L^1$ and $L^2$ each represents a moiety selected from the group consisting of —NHCO—, —CONH-, —O—, —S—, —NR—, wherein R is an alkyl group, —COO—, and —OCO—. It is particularly preferred that both of $L^1$ and $L^2$ are —NHCO—.

In the formula (I), W represents a quaternary ammonium group, preferably represented by formula (W). In the formula (W), $R^1$ and $R^2$ each represents a straight-chain or branched, saturated or unsaturated, aliphatic hydrocarbon group having from 1 to 6 carbon atoms, a substituted or unsubstituted cycloalkyl group, a substituted or unsubstituted aryl group, or a substituted or unsubstituted aralkyl group. $R^1$ and $R^2$ may be the same or different. Examples of the aliphatic hydrocarbon group include an alkyl group, an alkenyl group, an alkynyl group, and a cycloalkyl group. Examples of the alkyl group include a methyl group, an ethyl group, a propyl group, an isopropyl group, a butyl group, an isobutyl group, a sec-butyl group, a tert-butyl group, a pentyl group, an isopentyl group, a hexyl group and the like. Among these, a methyl group is preferred. Examples of the alkenyl group include a vinyl group, an allyl group, an crotyl group, an tiglyl group, a prenyl group, and the like. Particularly, those having from 2 to 5 carbon atoms are preferred. Examples of the alkynyl group include an ethynyl group, a propargyl group, and the like, with being those having from 2 to 5 carbon atoms preferred. The cycloalkyl group may have on its ring a substituent such as an alkyl group. Examples thereof include a cyclopropyl group, a cyclopentyl group, a cyclohexyl group, a 4-methylcyclohexyl group, 4-tert-butylcyclohexyl group, a cyclooctyl group, and the like. Particularly, those having 6 to 10 carbon atoms are preferred. The aryl group may be either monocyclic or polycyclic, for example, a phenyl group, a naphthyl group, and the like. The aralkyl group is exemplified by a benzyl group, a phenethyl group, and the like.

$R^1$ and $R^2$ may be bound to each other to form a nitrogen-containing heterocyclic group. Examples of the nitrogen-containing heterocyclic group include a pyridinium group, a pyrrolidinium group, a piperidinium group, a piperazinium group, and a morpholino group.

In the formula (W), X is a halogen atom such as Br, Cl, and I. Each of $Y^1$ and $Y^2$ is a linker for binding the carbodiimide group to B or —W—Z, and represents a direct bond or a straight-chain or branched alkylene group having from 1 to 20 carbon atoms in its main chain. Preferably, it is an alkylene group having from 1 to 4 carbon atoms in its main chain and optionally having a methyl group as a side chain. Examples thereof include a methylene group, an ethylene group, a trimethylene group, a 1-methyltrimethylene group, a 1-methyltetramethylene group, a 2,2-dimethyltrimethylene group, and the like. $Y^1$ and $Y^2$ may have in the main chain a moiety selected from the group consisting of —NHCO—, —CONH—, —O—, —S—, —NR—, wherein R is an alkyl group, —COO—, and —OCO—. Examples thereof include a moiety having plural alkylene groups which are bonded to each other via a bond arbitrarily selected from the group consisting of —NHCO—, —CONH—, —O—, —S—, —NR—, wherein R is an alkyl group, —COO—, and —OCO—.

In the formula (I), B represents a hydrogen atom, or a monovalent organic group, preferably, a tertiary amino group or a quaternary ammonium group. Suitable examples thereof include the following.

(i) A nitrogen-containing heterocyclic group in which a nitrogen atom may be quaternarized with a hydrogen atom, a saturated or unsaturated hydrocarbon group, an aryl group, an aralkyl group, or a digoxigenin-containing moiety represented by the above formula (Z), such as a pyridyl group, a pyridinium group, a pyrrolidyl group, a pyrrolidinium group, a piperidilyl group or a piperidinium group, particularly, a nitrogen atom may be quaternarized with a $C_1$–$C_{10}$ alkyl group, such as a methyl group, exemplified by 2-, 3-, or 4-pyridyl group, or pyridinium group, 2- or 3-pyrrolidyl group or pyrrolidinium group, and 2-, 3-, or 4-piperidilyl group or piperidinium group.

(ii) An amino group in which a nitrogen atom may be quaternarized with a hydrogen atom, a saturated or unsaturated hydrocarbon group, an aryl group, an aralkyl group, or a digoxigenin-containing moiety represented by the above formula (Z), particularly, an amino group in which a nitrogen atom may be quaternarized with a $C_1$–$C_{10}$ alkyl group such as a methyl group, or a digoxigenin-containing moiety represented by the above formula (Z), specifically exemplified by a dimethylamino group, a diethylamino group, and a diisopropylamino group.

(iii) A heterocyclic tertiary amino group, a heterocyclic tertiary or quaternary ammonium group, represented by the following formula:

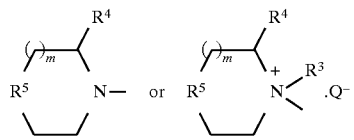

wherein $R^3$ and $R^4$ each represents a hydrogen atom or a $C_1$–$C_{10}$ straight-chain or branched aliphatic hydrocarbon group, or a substituted or unsubstituted aryl group or a substituted or unsubstituted aralkylgroup, particularly, a $C_1$–$C_{10}$ alkyl group, a phenyl group, and a phenyl group substituted with a $C_1$—$C_{10}$ alkyl group. Q represents an anion, such as a sulfate ion, an alkylsulfate ion, an arylsulfate ion, a halosulfate ion, a halide ion, and the like. $R^5$ represents an oxygen atom, a sulfur atom, or a methylene group. m is 0 or 1.

Specifically, a group represented by the following formula:

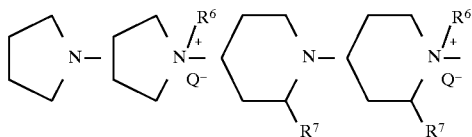

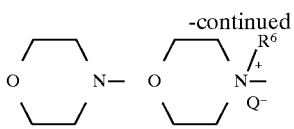

wherein $R^6$ and $R^7$ each represents a hydrogen atom, a $C_1$–$C_{10}$ alkyl group, or a phenyl group, or a phenyl group substituted with a $C_1$–$C_{10}$ alkyl group.

B may be the same as or different from a monovalent organic group represented by —W—Z in the formula (I) (W and Z have the same meaning as defined in the formula (I)). When it is the same, it can be a compound having a structure symmetrical about the carbodiimide group in the formula (I).

A particularly preferable compound of the carbodiimide group-containing digoxigenin derivative of the present invention is represented by the following formula (II):

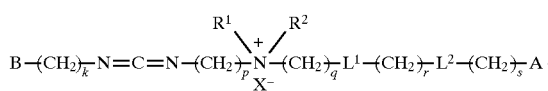

wherein k and p each represents an integer of from 1 to 12; $L^1$, $L^2$ q, r, and s each has the same meaning as defined in the formula (L); A and B have the same meaning as defined in the formula (I) and the formula (Z), respectively; and $R^1$ and $R^2$ each has the same meaning as defined in the formula (W).

Specifically, it is exemplified by the compound represented by the following formula:

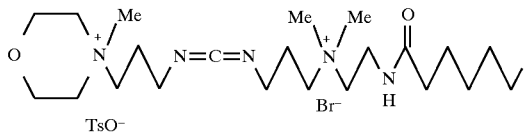

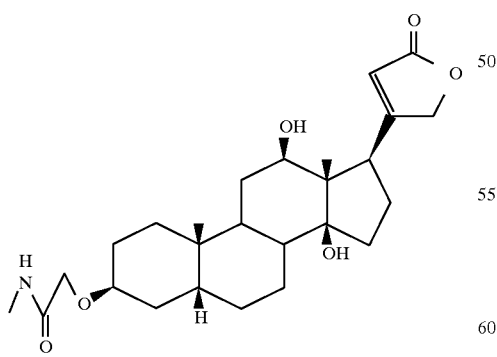

(2) Process for producing the carbodiimide group-containing digoxigenin derivative of the invention The digoxigenin derivative represented by the above formula (I) according to the present invention can be produced by a method comprising a step of reacting the carbodiimide compound represented by the above formula (III) with the halogen-containing digoxigenin derivative represented by the above formula (IV). Namely, the carbodiimide compound represented by the formula (III) has at its terminal end a substituted or unsubstituted amino group (W'), which is reacted with a halogen atom (X) at the terminal end of the digoxigenin derivative represented by the formula (IV) to thereby bind to each other.

B, $Y^1$, and $Y^2$ in the formula (III), and Z in the formula (IV) have the same meaning as defined in the above formula (I). The carbodiimide compound represented by the formula (III) and the halogen-containing digoxigenin derivative represented by the formula (IV) are arbitrarily selected depending on the structure of a desired carbodiimide group-containing digoxigenin derivative.

Specific examples of the carbodiimide compound represented by the formula (III) include N-3,3-dimethylaminopropyl-N'-3-(4-morpholino)propylcarbodiimide, 1-ethyl-3,3-dimethylaminopropylcarbodiimide,

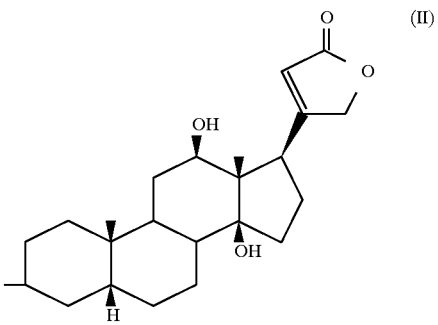

bis-(3,3-dimethylaminopropyl)carbodiimide, and the like. These carbodiimide compounds can be obtained by reacting an amino group-containing isothiocyanate compound ("a" in the reaction formula) with an amine compound ("b") to synthesize a thiourea compound ("c"), and subjecting the resulting thiourea compound to the conventional desulfurization reaction using as a catalyst mercury oxide, lead oxide, and the like.

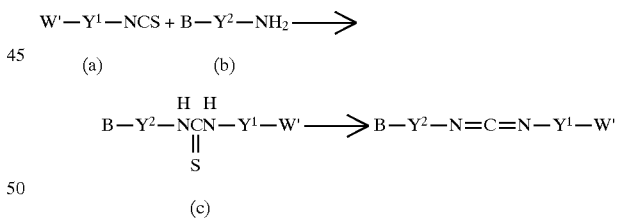

The amino group-containing isothiocyanate and the amine compound used in this reaction can be arbitrarily selected depending on the structure of a desired carbodiimide compound. Examples of the amino group-containing isothiocyanate compound include 3,3-dimethylaminopropyl-isothiocyanate, 3-($^4$-morpholino)propylisothiocyanate, and the like. As the amine compound, 4-(3-aminopropyl)morpholine, N,N-dimethylpropane diamine, and the like are exemplified.

Examples of the halogen-containing digoxigenin derivative represented by the formula (IV) include digoxigenin bromide, digoxigenin iodide, digoxigenin chloride, and the like, represented by the following formula:

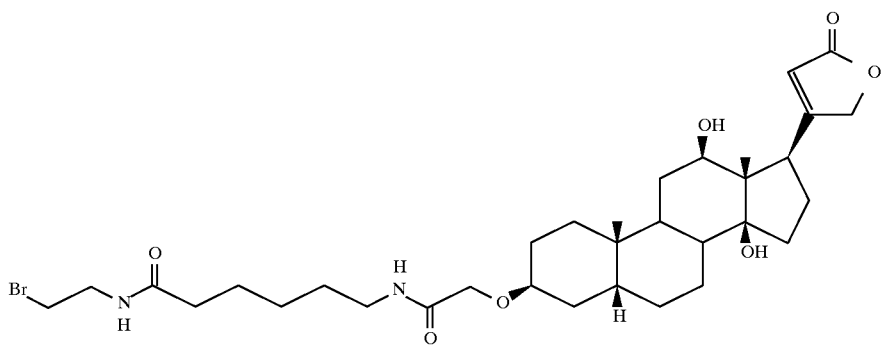

These halogen-containing digoxigenin derivative can be obtained by reacting an ester derivative of digoxigenin, such as digoxigenin succinimide, digoxigenin p-nitrophenol, and the like, with a halogenating reagent, such as 2-bromoethylamine, 2-iodoethylamine, 2-chloroethylamine, and the like, using the conventional method. In this case, it is preferable that the ester derivative of digoxigenin is dissolved in a mixed solvent containing a buffer such as sodium borate buffer and the like, prior to the reaction.

used as the label in the nucleic acid detection method and immunoassay. In this case, the carbodiimide group-containing digoxigenin derivative of the present invention can be brought into contact with a nucleic acid such as DNA or a protein such as antigen or antibody to be labelled by mixing these compounds in a solvent to bind to each other. Namely, digoxigenin, which is a highly sensitive detection reagent, can be attached as the label to a substance to be labelled including a nucleic acid or a protein by binding the

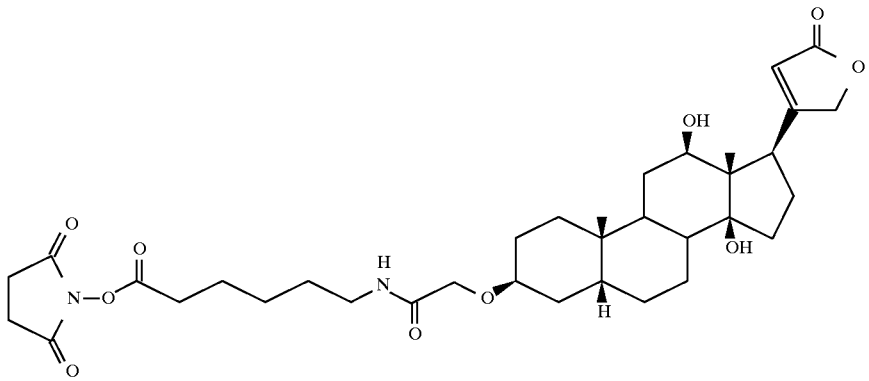

Each step of these reactions can be carried out by the known methods using a solvent usually used such as dimethylformamide (DMF), acetone, benzene, ether, dichloromethane, and the like.

In the present invention, the thus-obtained carbodiimide compound represented by the formula (III) is reacted with the halogen-containing digoxigenin derivative represented by the formula (IV) using a solvent usually used such as dimethylformamide, dichloromethane, dimethylsulfoxide (DMSO) and the like, for example, through the reaction steps represented by the following formulae, to obtain the carbodiimide group-containing digoxigenin derivative.

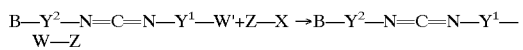

When the portion of B in the resulting carbodiimide group-containing digoxigenin derivative represented by the formula (I) is a tertiary amino group, the B portion can be converted to a quaternary ammonium group by further reacting the derivative with methyl p-toluenesulfonate (TsOMe), methyl iodide, ethyl iodide, and the like, in a solvent such as dimethylformamide to improve its water-solubility.

The thus-obtained carbodiimide group-containing digoxigenin derivative of the present invention can be suitably carbodiimide group which is highly-reactive with a nucleic acid base, of the carbodiimide group-containing digoxigenin derivative of the present invention to the nucleic acid or the protein. The carbodiimide group is preferably contacted under its reactive condition, for example, under alkaline conditions such as about pH 7.5 to 8.5.

(3) Nucleic acid detection method of the invention

The carbodiimide group-containing digoxigenin derivative of the present invention can be used as the label in the nucleic acid detection method by hybridization using a labelled nucleic acid. Namely, the nucleic acid labelled with the carbodiimide group-containing digoxigenin derivative can be used as a probe for hybridization. The nucleic acid to be assayed can be detected by allowing the nucleic acid to be assayed to hybridize with the probe to form a nucleic acid-nucleic acid hybrid, removing free probe from the system, and detecting the label contained in the hybrid. In the present invention, the carbodiimide group-containing digoxigenin derivative used as the label can be detected using an enzyme-bound anti-digoxigenin antibody. The nucleic acid to be assayed is usually immobilized on a membrane such as nylon membrane or nitrocellulose, prior to use.

For hybridization in the nucleic acid detection method according to the present invention, any common nucleic acid hybridization method can be applied, including colony hybridization, plaque hybridization, dot blot hybridization, southern hybridization, northern hybridization, and the like, except for using the carbodiimide group-containing digoxigenin derivative as the label for a nucleic acid probe. The nucleic acid to be assayed may be either DNA or RNA. The nucleic acid used as a probe may also be DNA or RNA.

Labeling of a nucleic acid used as a probe can be preferably carried out by labeling polynucleotide or oligonucleotide using the above method. Alternatively, labelled nucleotide can be incorporated into polynucleotide or oligonucleotide by the polymerase reaction.

(4) Immunoassay of the invention

The above-described carbodiimide group-containing digoxigenin derivative of the present invention can be used as the label in immunoassay using a labelled antigen or a labelled antibody.

When an antigen is to be assayed, it can be detected by labeling an antibody which is specifically bound to the antigen, forming an antigen-antibody complex, then removing free antibody from the system, and detecting the label contained in the complex. In the present invention, the carbodiimide group-containing digoxigenin derivative to be used as the label can be detected by using an enzye-bound anti-digoxigenin antibody. Alternatively, a first antibody which is specifically bound to the antigen is immobilized, and allowed to bind to the antigen, then a labelled second antibody which is specifically bound to the antigen is further allowed to bind thereto. In this case, the first antibody and the second antibody may be the same polyclonal antibody, or different monoclonal antibodies. Further, one of them may be polyclonal antibody, and the other may be monoclonal antibody. In each case, alternatively, an unlabelled antibody may be used in place of a labelled antibody, an antigen is allowed to bind thereto, and a labelled second antibody which is specifically bound to the antibody is further allowed to bind thereto. Immunoglobulin derived from an animal used in preparing an antibody can be used to immunize a different animal to obtain the second antibody.

When an antibody is to be assayed, it can be detected by labeling an antigen which is specifically bound to the antibody, forming an antigen-antibody complex, then removing free antigen from the system, and detecting the label contained in the complex. When an antibody which is specifically bound to the antibody to be assayed can be obtained, it may be labelled and used to form an antibody-antibody complex.

Any commonly used procedure of immunoassay can be applied to the immunoassay of the present invention, except for using the carbodiimide group-containing digoxigenin derivative as the label for an antigen or an antibody. Immobilization of an antigen or an antibody, antigen-antibody reaction, washing procedure, and the like can be carried out in the same manner as in the commonly used methods. Any method of immunoassay including the direct method, the indirect method, the competitive method, and the like can be applied.

EXAMPLE

In the following, Examples of the present invention is provided.

PRODUCTION EXAMPLE

An example of the process for producing the carbodiimide group-containing digoxigenin derivative of the present invention is illustrated with reference to the reaction formulae.

(1) Synthesis of thiourea compound (Reaction formula (1))

In 15 ml of dry methylene chloride was dissolved 1.4 g (10 mmol) of 3-dimethylaminopropylisothiocyanate and the mixture was cooled in ice. After adding in the mixture 1.4 g (10 mmol) of 4-(3-aminopropyl)morpholine, the mixture was stirred overnight at room temperature. Water was added to the reaction mixture, which was subjected to extraction with methylene chloride (5 ml×3 times). After dried over anhydrous potassium carbonate, the resulting mixture was concentrated to obtain 2.7 g (yield: 98%) of N-3-dimethylaminopropyl-N'-3-(4-morpholino)propylthiourea (Compound-1 in the following reaction formula (1)).

Reaction formula (1)

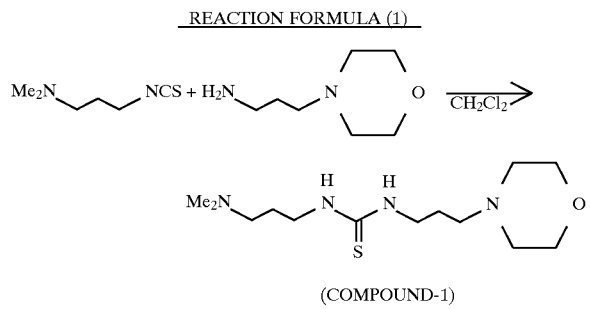

(COMPOUND-1)

(2) Synthesis of carbodiimide compound (Reaction formula (2))

In 35 ml of acetone was dissolved 2.7 g (10 mmol) of N-3-dimethylaminopropyl-N'-3-(4-morpholino)propylthiourea (Compound-1). Further, 4.2 g (20 mmol) of mercury oxide was added thereto, and the resulting mixture was stirred for 2 hours under reflux. Then, the reaction mixture was allowed to cool and filtered. The solvent was distilled off to obtain a crude product. This product was distilled under reduced pressure to obtain 1.5 g (yield: 60%) of N-3-dimethylaminopropyl-N'-3-(4-morpholino)propylcarbodiimide (Compound-2). Its boiling point (b.p.) was from 125 to 128° C./0.2 mmHg.

Reaction formula (2)

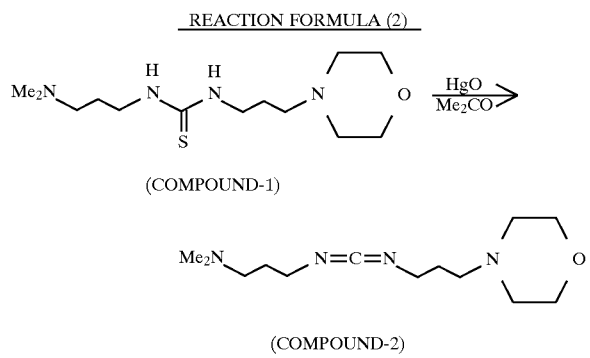

(3) Synthesis of digoxigenin bromide (Reaction formula (3))

20 mg (0.03 mmol) of a digoxigenin succinimide ester derivative was dissolved in a mixed solution of 0.5 ml of dimethylformamide (DMF) and 0.5 ml of 1N sodium borate buffer (pH 8.5). To this mixture was added 6 mg (0.03 mmol) of a hydrobromide salt of 2-bromoethylamine and the resulting mixture was allowed to react at room temperature for 18 hours with gently shaking. Then, the resulting reaction mixture was extracted with chloroform (1 ml) three times and washed with a saturated sodium chloride solution once. After dried over magnesium sulfate, the solvent was distilled off to obtain 21 mg of a solid reaction mixture. This reaction mixture was purified using a silica gel column to give 10 mg of digoxigenin bromide (Compound-3).

Reaction formula (3)

propylcarbodi imide (Compound-2) was added thereto, followed by stirring at room temperature for 18 hours. After the reaction solvent was distilled off, the remaining reaction mixture was dissolved in a small amount of dimethylforma-

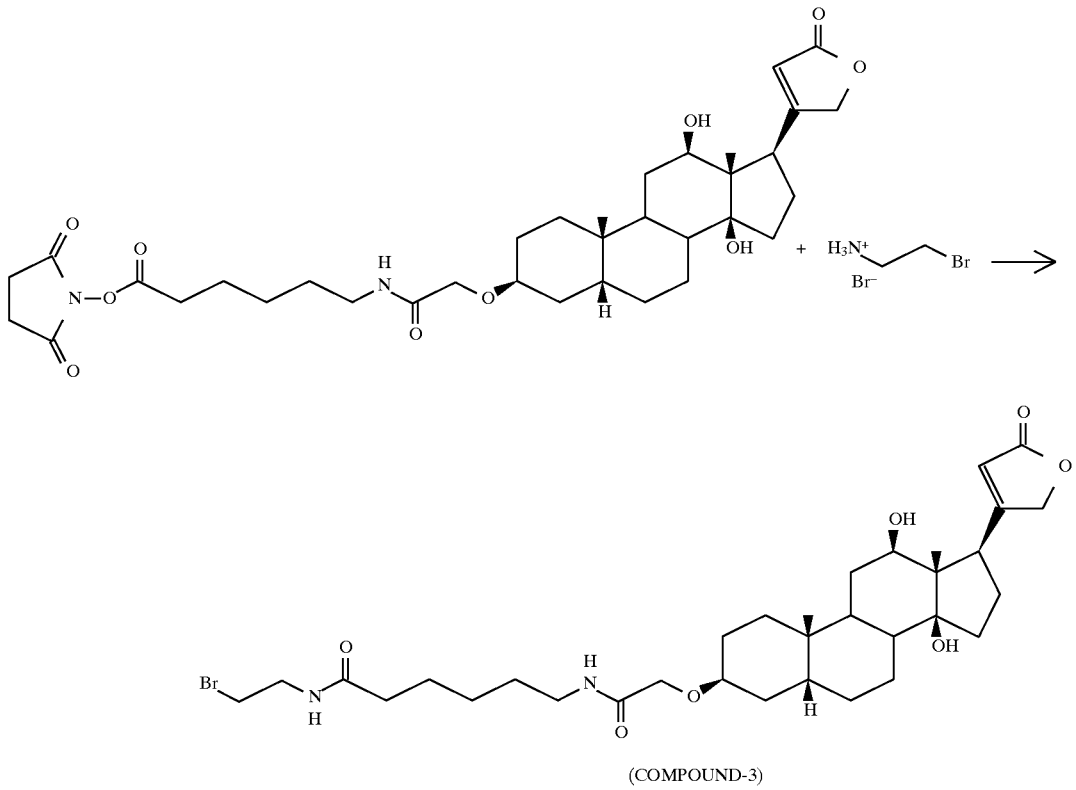

(4) Synthesis of carbodiimide group-containing digoxigenin derivative (Reaction formula (4))

10 mg (0.015 mmol) of digoxigenin bromide (Compound-3) was dissolved in 3 ml of dimethylformamide. Then, 2 ml of dimethylformamide solution containing 10 mg (0.04 mmol) of N-3-dimethylaminopropyl-N'-3-(4-morpholino)

mide and the resulting mixture was added dropwise to dimethyl ether. The precipitated white crystal was separated by filtration and dried to obtain 10 mg of a carbodiimide group-containing digoxigenin derivative (Compound-4).

Reaction formula (4)

REACTION FORMULA (4)

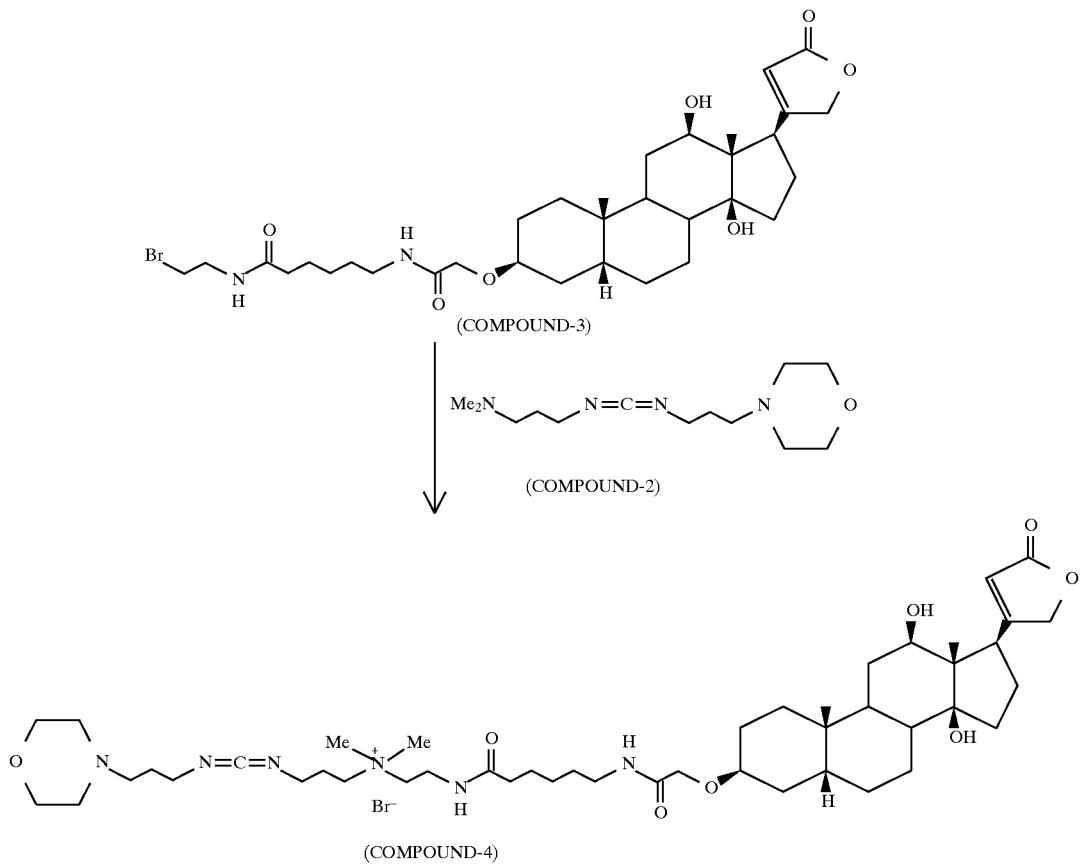

(5) Introduction of quaternary ammonium group into the carbodilmide group-containing digoxigenin derivative (Reaction formula (5))

10 mg (0.01 mmol) of the carbodiimide group-containing digoxigenin derivative (Compound-4) was dissolved in 3 ml of dimethylformamide. Then, 2 ml of dimethylformamide solution containing 10 mg (0.05 mmol) of methyl p-toluenesulfonate (TsOMe), followed by stirring at room temperature for 18 hours. After the reaction solvent was distilled off, the remaining reaction mixture was dissolved in a small amount of dimethylformamide and the resulting mixture was added dropwise into dimethyl ether. The precipitated white crystal was separated by filtration and dried to obtain 5 mg of a carbodiimide group-containing digoxigenin derivative having a quaternary ammonium group (Compound-5).

Reaction formula (5)

REACTION FORMULA (5)

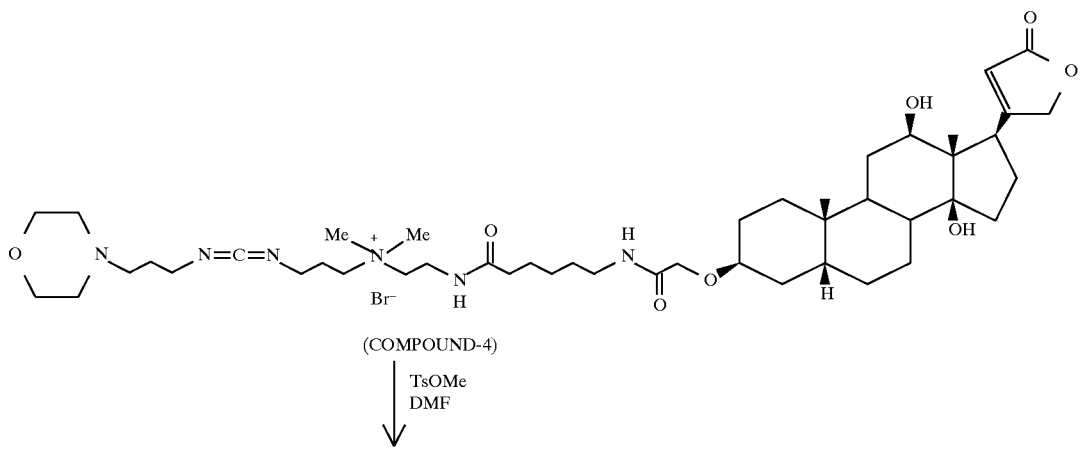

-continued
REACTION FORMULA (5)

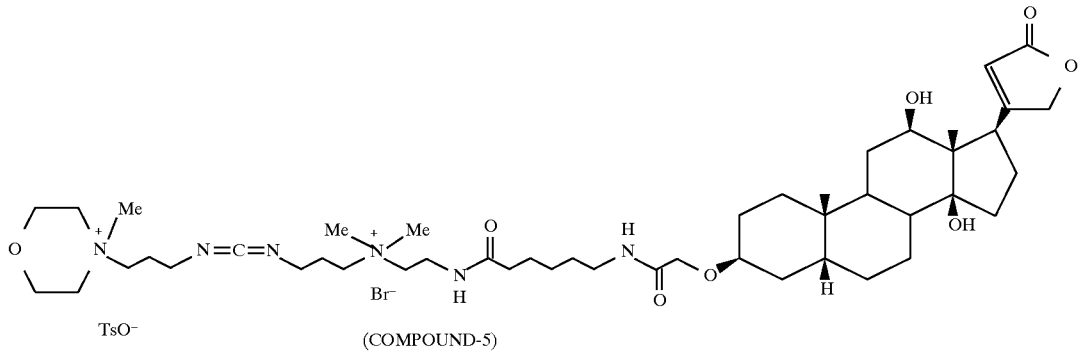

(COMPOUND-5)

EXAMPLE 1

(1) Labeling of DNA with digoxigenin

The reaction mixture (phage DNA (replicative form of M13mp18: Takara Shuzo) 1 μg:0.1M borate buffer (pH 8.5):0.25% SDS:0.1M carbodiimide group-containing digoxigenin derivative (Compound-5)) was incubated at 85° C. for 1 minute to label DNA with digoxigenin. Then, in order to remove unreacted carbodiimide group-containing digoxigenin derivative, the reaction mixture was mixed with 3M sodium acetate in a 1/9 amount of the sample and cold ethanol in a double amount of the sample, and the resulting mixture was allowed to stand at −80° C. for 45 minutes. The mixture was centrifuged at 4° C. at 12,000 rpm for 15 minutes using a centrifuge (H-1500FR Model, Kokusansha) to remove the upper layer. Then, 500 μl of 70% ethanol was added to the residue, and centrifugation was further carried out at 4° C. at 12,000 rpm for 1 minute and 30 seconds. After removing the upper layer, the precipitate was dissolved in 100 μl of sterilized water, and the mixture was kept at −20° C. The thus-obtained digoxigenin-labelled DNA was used for the dot blotting detection as described below.

(2) Immobilization of DNA

A DNA concentration of the digoxigenin-labelled DNA solution was determined using a UV detector (UV-VISIBLE RECORDING SPECTROPHOTOMETER UV-2100, Shimadzu Seisakusho). Then, serial dilutions of the digoxigenin-labelled DNA (10 pg/μl, 1 pg/μl, 100 fg/μl, 10 fg/μl, 1 fg/μl) were prepared and 1-μl aliquots of each dilution was dot blotted on nylon membrane (Hybond N+, Amersham). After drying the membrane, Auto Cross Link (DNA immobilization program) was carried out using UV stratalinkerTM (STRATAGENE) to immobilize DNA on the membrane.

(3) Chemiluminescence

The membrane was immersed in buffer A solution (0.2M NaCl:0.1M Tris-HCl (pH 7.5) 0.05% Triton-X 100) for 1 minute. Then, the above membrane was put into a plastic bag (Hybribag, tradename: BRL (Bethesda Research Laboratories)), buffer B solution (3% BSA+buffer A solution) was added thereto at a ratio of 5 ml per 100 cm² of the membrane, and the bag was allowed to stand at room temperature for 30 minutes.

Then, the above membrane was transferred to a new Hybribag. Separately, a solution was prepared so as to contain 2.5 μl of anti-digoxigenin antibody-alkaline phosphatase conjugate (Anti DIG alkaline phosphatase conjugate: Boehringer Mannheim Biochemica) per ml of buffer A solution. This solution was added into the bag at a ratio of 1 ml per 100 cm² of the membrane, and the bag was allowed to stand at room temperature for 25 minutes. The membrane was taken out from the Hybribag, washed with 100 ml of buffer A solution for 10 minutes three times, and immersed in 50 ml of buffer C solution (0.1M NaCl:0.1M Tris-HCl (pH 9.5):'50 mM MgCl₂) for 5 minutes. Then, the membrane was put into the Hybribag again.

A solution was prepared so as to contain 32 μl of NBT (Nitroblue tetrazolium chloride) and 16 μl of X-phosphate (5-bromo-4-chloro-3-indolyl phosphate) per 5 ml of buffer C solution and added at a ratio of 5 ml per 100 cm² of the membrane to allow it to color in the dark. The membrane was washed with sterilized water and dried for preservation.

As a result, DNA labelled with the digoxigenin derivative of the present invention can be detected at the level of 1 fg. On the other hand, a DNA labelled using DIG DNA Labeling and detection Kit by the random primer method which was allowed to color in the same manner as described above could be detected to the level of only 10 fg.

EXAMPLE 2

Using the carbodiimide group-containing digoxigenin derivative of the present invention as the label, a protein was detected by the antigen-antibody reaction using a membrane in the following manner.

(1) Labeling of protein with digoxigenin

The reaction mixture [anti-rabbit IgG antibody (goat) (VECTER LABORATORIES) 100 μg : 0.1M borate buffer (pH 9.0) : 0.1M carbodiimide group-containing digoxigenin derivative (Compound-5)] was allowed to stand on ice for 10 minutes to label a protein with digoxigenin. Them, 10% SDS was added thereto so as to give a concentration of 0.3 % based on the total amount and the mixture was centrifuged at 5,000 rpm for 15 minutes using microtube for centrifugation (Ultrafree C3LGC, tradename: Millipore) to remove unreacted carbodiimide group-containing digoxigenin derivative. Then, 50 μl each of 100 mM sodium phosphate buffer (pH 7.6) and 50 mM NaCl were added to a filter cup to centrifuge at 5,000 rpm for 10 minutes. After repeating the same procedure, the residue was transferred to an Eppendorf tube and 100 mM sodium phosphate buffer (pH 7.6) and 50 mM NaCl were added thereto to give a 0.1M solution. The resulting solution was kept at 4° C.

(2) Immobilization of IgG on the membrane

Ten-fold serial dilutions of rabbit IgG were prepared using buffer A solution in the range from 100 pg/μl to 1 fg/μl. 1-μl aliquots of each IgG dilutions were dot blotted on PBDF (polyvinylidene fluoride) membrane (Millipore) and dried at 37° C. for 10 minutes to immobilize IgG on the membrane. Then, the resulting IgG-immobilized membrane was immersed in buffer B solution and allowed to stand for 30 minutes to effect blocking.

(3) Antigen-antibody reaction

The membrane was taken out from the buffer B solution and immersed in the reaction solution with shaking with a shaker at room temperature for 30 minutes. The reaction solution used have the following composition: buffer B solution, 10 ml; 4 pg/μl digoxigenin-labelled anti-rabbit IgG, 10 μl. The digoxigenin-labelled anti-rabbit antibody used was obtained by the method described in the (1) above.

(4) Removal of unreacted digoxigenin-labelled anti-rabbit antibody

The unreacted digoxigenin-labelled anti-rabbit antibody which did not react with the immobilized antibody was removed by carrying out the washing procedure three times wherein the reacted membrane was immersed in buffer A solution with shaking at room temperature for 5 minutes.

(5) Chemiluminescence

The membrane was put into Hybribag (BRL) and buffer B solution was added to the bag at a ratio of 5 ml per 100 cm² of the membrane. The bag was allowed to stand at room temperature for 30 minutes. Then, the membrane was transferred to a new Hybribag. Separately, a solution was prepared so as to contain 2.5 μl of Anti DIG alkaline phosphatase conjugate (Boehringer Mannheim Biochemica) per 1 ml of buffer B solution. This solution was added into the bag at a ratio of 1 ml per 100 cm² of the membrane, and the bag was allowed to stand at room temperature for 25 minutes. The membrane was taken out from the Hybribag, washed with 100 ml of buffer A solution for 10 minutes three times, and immersed in 50 ml of buffer C for 5 minutes. Then, the membrane was put into the Hybribag again. A solution was prepared so as to contain 32 μl of NBT and 16 μl of X-phosphate (5-bromo-4-chloro-3-indolyl phosphate) per 5 ml of buffer C solution and added at a ratio of 5 ml per 100 cm² of the membrane to effect coloration for 1 hour in the dark. The membrane was washed with sterilized water and dried for preservation.

As a result, the protein labelled with the digoxigenin derivative of the present invention can be detected at the level of 1 pg. On the other hand, a protein labelled with N-hydroxysuccuinimide digoxigenin-3-o-methylcarbonyl-ε-aminocaproate (Boehringer Mannheim Biochemica) which was allowed to color in the same manner as described above could be detected to the level of only 10 pg.

Thus, the carbodiimide group-containing digoxigenin derivative of the present invention enables highly sensitive nucleic acid detection and immunoassay with simple labeling procedure.

What is claimed is:

1. A carbodiimide group-containing digoxigenin derivative represented by the formula (I):

$$B-Y^2-N=C=N-Y^1-W-Z \quad (I)$$

wherein Z represents a digoxigenin-containing moiety represented by the formula (Z):

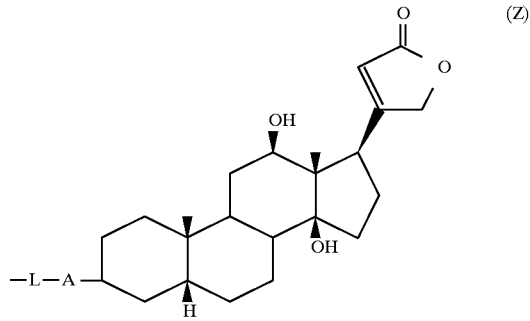

wherein A represents —O—, —COO—, or —NHCOO—;
L represents a straight-chain or branched alkylene group which may have a moiety in the main chain selected from the group consisting of —NHCO—, —CONH—, —O—, —S—, —NR—,
wherein R is an alkyl group, —COO—, and —OCO—;
W represents a quaternary ammonium group;
$Y^1$ and $Y^2$ each represents a direct bond or a straight-chain or branched alkylene group having from 1 to 20 carbon atoms in its main chain and optionally having in the main chain a moiety selected from the group consisting of —NHCO—, —CONH—, —O—, —S—, —NR—, wherein R is an alkyl group, —COO—, and —OCO—; and
B represents a hydrogen atom or a monovalent organic group which may be the same as or different from that represented by —W—Z in the formula (I).

2. The carbodiimide group-containing digoxigenin derivative as claimed in claim 1, wherein W in the formula (I) is a quaternary ammonium group represented by the formula (W):

wherein $R^1$ and $R^2$ each represents a straight-chain or branched, saturated or unsaturated aliphatic hydrocarbon group having from 1 to 6 carbon atoms, a substituted or unsubstituted cycloalkyl group, a substituted or unsubstituted aryl group, a substituted or unsubstituted aralkyl group, or a nitrogen-containing heterocyclic group formed by $R^1$ and $R^2$ which are bound to each other; and
X represents a halogen atom.

3. The carbodiimide group-containing digoxigenin derivative as claimed in claim 1, wherein B in the formula (I) represents a tertiary amino group or a quaternary ammonium group.

4. The carbodiimide group-containing digoxigenin derivative as claimed in claim 1, wherein B in the formula (I) is a monovalent organic group represented by —W—Z, wherein W and Z each has the same definition as in the formula (I).

5. The carbodiimide group-containing digoxigenin derivative as claimed in claim 1, wherein the derivative represented by the formula (I) is a compound represented by the formula (II):

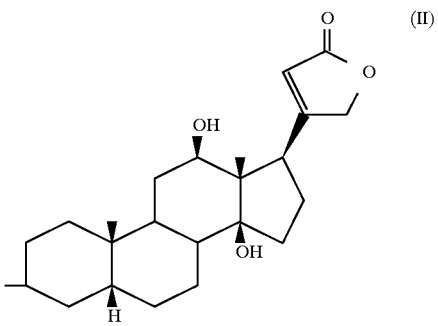

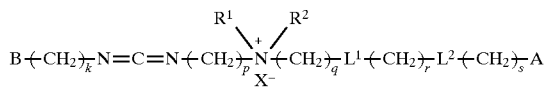

wherein k, p, q, r and s each represents an integer of from 1 to 12;

$L^1$ and $L^2$ each represents a moiety selected from the group consisting of —NHCO—, —CONH—, —O—, —S—, —NR—, wherein R is an alkyl group, —COO—, and —OCO—; A and B each has the same meaning as those defined in the formulae (I) and (Z);

$R^1$ and $R^2$ each represents a straight-chain or branched, saturated or unsaturated aliphatic hydrocarbon group having from 1 to 6 carbon atoms, a substituted or unsubstituted cycloalkyl group, a substituted or unsubstituted aryl group, a substituted or unsubstituted aralkyl, or a nitrogen-containing heterocyclic group formed by $R^1$ and $R^2$ which are bound to each other; and X represents a halogen atom.

6. A process for producing the carbodiimide group-containing digoxigenin derivative as claimed in claim 1 which comprises a step of reacting a carbodiimide compound represented by the formula (III):

$$B-Y^2-N=C=N-Y^1-W' \quad \text{(III)}$$

wherein B, $Y^1$ and $Y^2$ each has the same meaning as those defined in the formula (I); and W' represents a substituted or unsubstituted amino group, with a digoxigenin halide represented by the formula (IV):

$$Z-X \quad \text{(IV)}$$

wherein Z has the same meaning as that defined in the formula (I); and X represents a halogen atom.

7. A method of detecting a nucleic acid by hybridization using the labelled nucleic acid, wherein the carbodiimide group-containing digoxigenin derivative as claimed in claim 1 is used as the label.

8. A method of immunoassay using a labelled antigen or a labelled antibody, wherein the carbodiimide group-containing digoxigenin derivative as claimed in claim 1 is used as the label.

* * * * *